(12) United States Patent
Fry

(10) Patent No.: US 9,592,059 B2
(45) Date of Patent: Mar. 14, 2017

(54) BATTLE APPLICATION TOURNIQUET FOR LIMB

(71) Applicant: Rick Shawn Fry, Chesapeake, VA (US)

(72) Inventor: Rick Shawn Fry, Chesapeake, VA (US)

( * ) Notice: Subject to any disclaimer, the term of this patent is extended or adjusted under 35 U.S.C. 154(b) by 103 days.

(21) Appl. No.: 14/536,655

(22) Filed: Nov. 9, 2014

(65) Prior Publication Data

US 2016/0128700 A1   May 12, 2016

(51) Int. Cl.
*A61B 17/132*   (2006.01)

(52) U.S. Cl.
CPC .................. *A61B 17/1322* (2013.01)

(58) Field of Classification Search
CPC .............. A61B 17/132; A61B 17/1322; A61B 17/1325; A61B 17/1327; A61B 2017/0404; A61B 2017/0496; A61F 2013/00463; A61F 2013/00468
See application file for complete search history.

(56) References Cited

U.S. PATENT DOCUMENTS

| | | | | |
|---|---|---|---|---|
| 34,112 A * | 1/1862 | Lambert | ............ | A61B 17/1327 24/186 |
| 1,447,967 A * | 3/1923 | Rutledge | ................ | A44B 11/25 24/163 R |
| 2,893,394 A * | 7/1959 | Wilhelm | ............ | A61B 17/1327 24/200 |
| 5,451,234 A * | 9/1995 | Wassermann | ...... | A61B 17/1327 606/203 |
| 5,792,173 A * | 8/1998 | Breen | ................... | A61B 17/135 606/1 |
| 5,799,650 A * | 9/1998 | Harris | ................ | A61B 17/1325 128/107.1 |
| 2003/0028215 A1* | 2/2003 | Brooks | .............. | A61B 17/1327 606/203 |
| 2010/0057120 A1* | 3/2010 | Kirkham | ............ | A61B 17/1322 606/203 |
| 2010/0286724 A1* | 11/2010 | Rose | ................... | A61B 17/1322 606/203 |
| 2011/0307004 A1* | 12/2011 | Johnson | ............. | A61B 17/1322 606/203 |
| 2014/0031864 A1* | 1/2014 | Jafari | ................. | A61B 17/0401 606/232 |

* cited by examiner

*Primary Examiner* — Alexander Orkin
(74) *Attorney, Agent, or Firm* — Bradley Goldizen

(57) ABSTRACT

The present invention relates generally to an emergency tourniquet for rapidly and easily reducing or stopping blood flow to an injured limb. The tourniquet utilizes a closed loop system that is formed by passing a portion of a twistable strap, which comprises the loop, through a side opening in a buckle and cinching the strap tightly above an injury and thereafter twisting the strap. Otherwise, a loop may be formed and the injured limb passed through the loop prior to tightening it about the injured limb. The buckle includes an elongated opening that accepts an end or edge of the twistable strap. A free end of the twistable strap passes into a J-hook opening and is secured therein. The strap is then twisted and a notch in the buckle is hooked on an edge of the twistable strap. Bulbous regions are provided on either end of the buckle. A base plate may also be included for further securing the buckle in place to maintain the tourniquet in place until it can be removed by a competent medical professional.

11 Claims, 9 Drawing Sheets

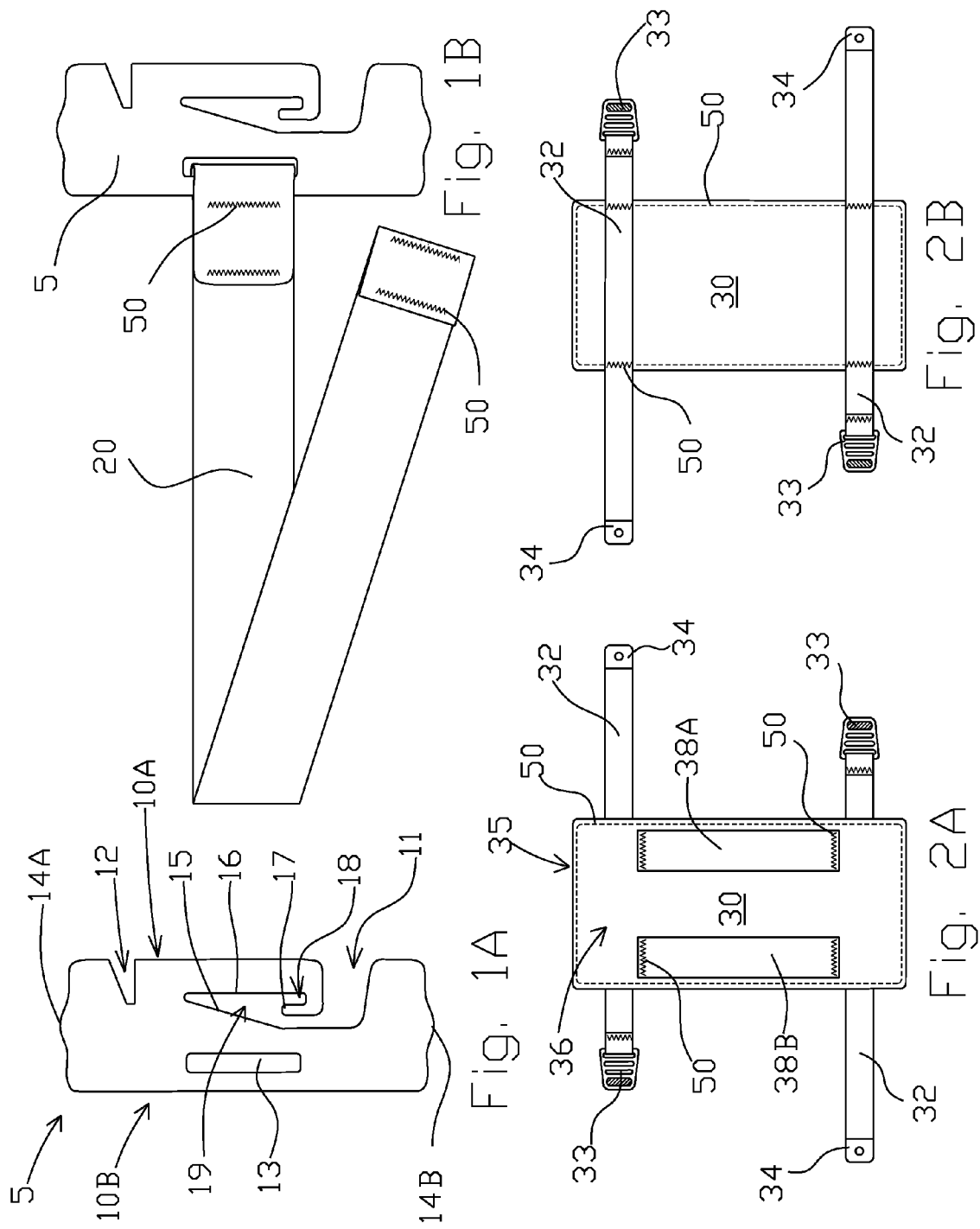

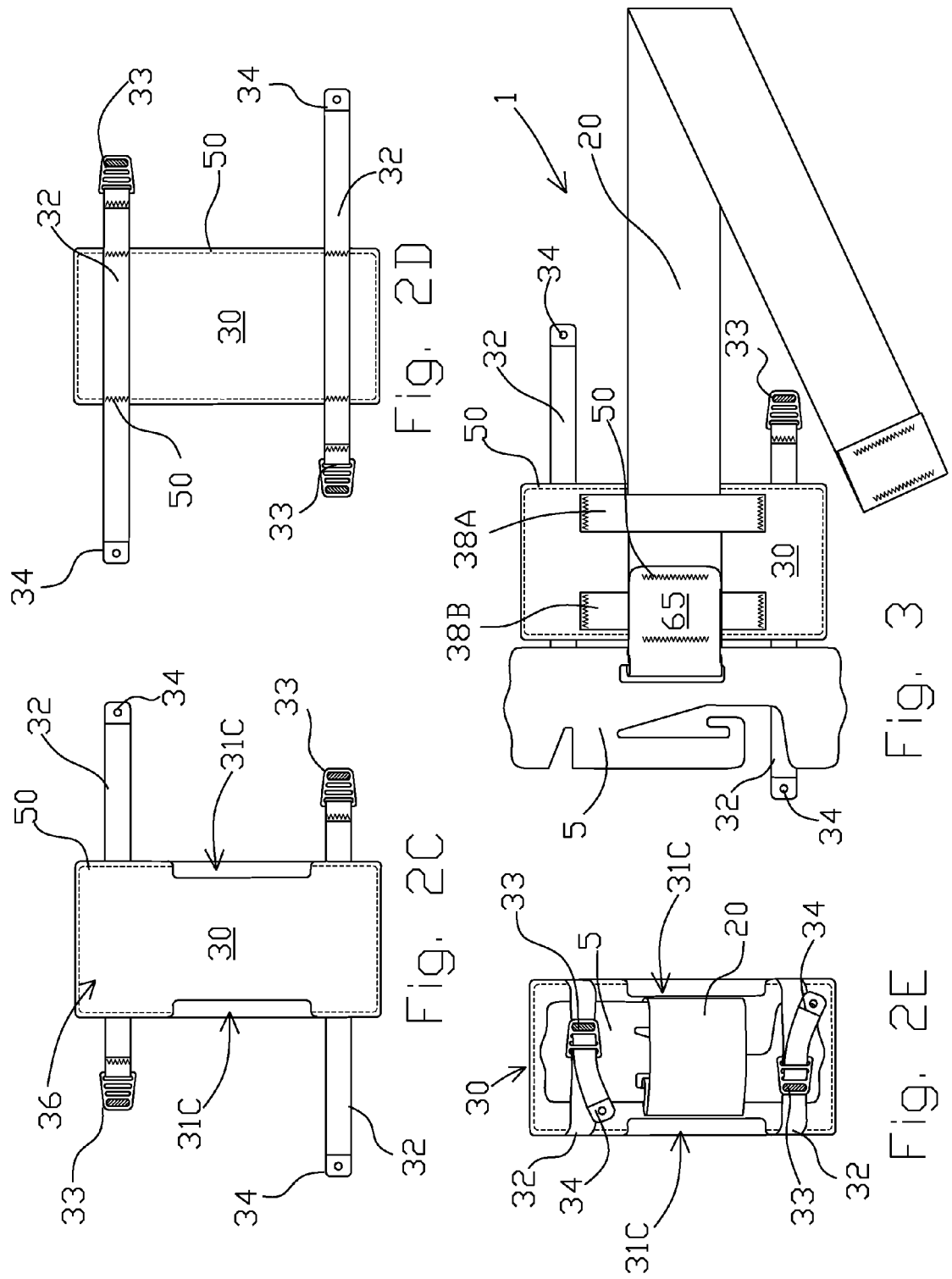

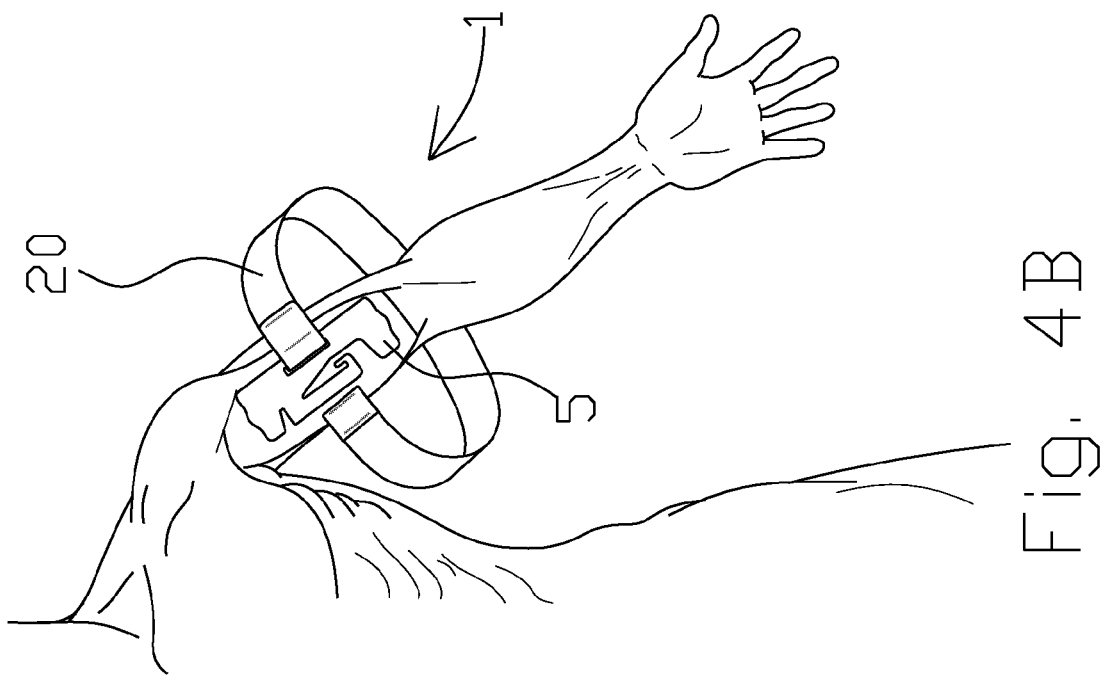
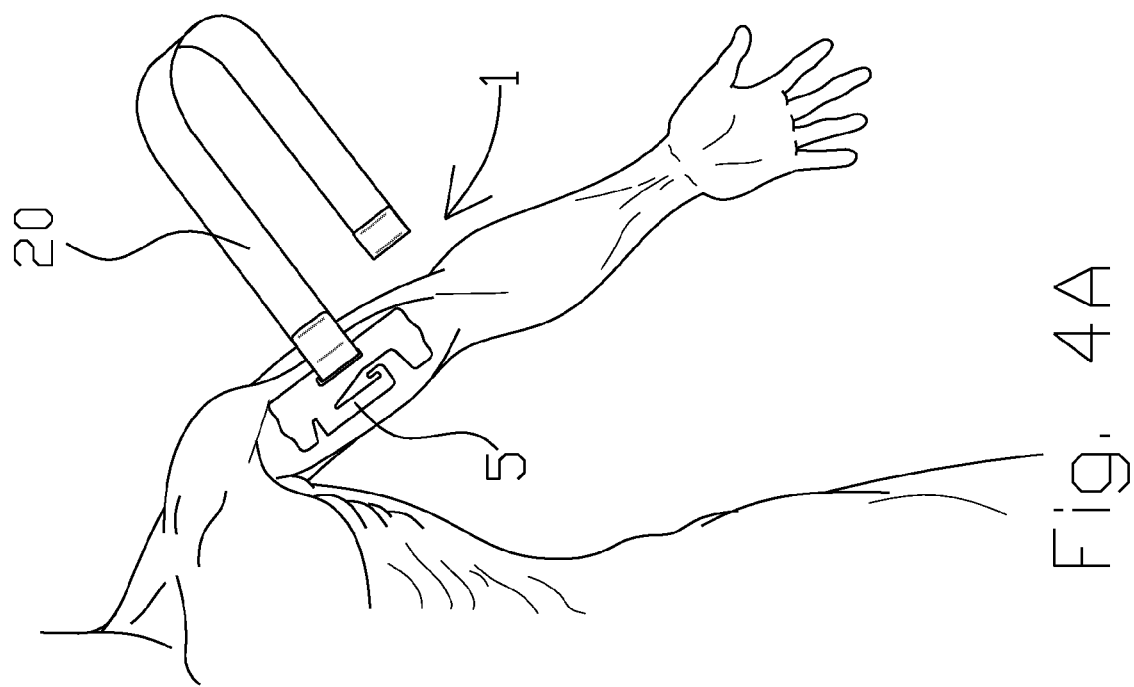

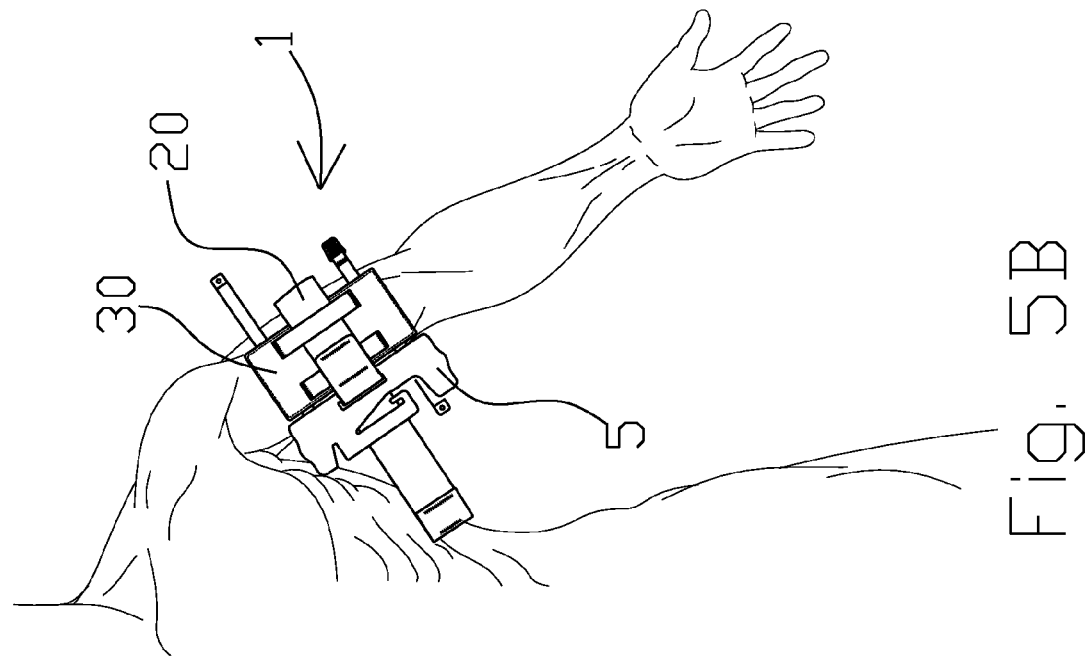
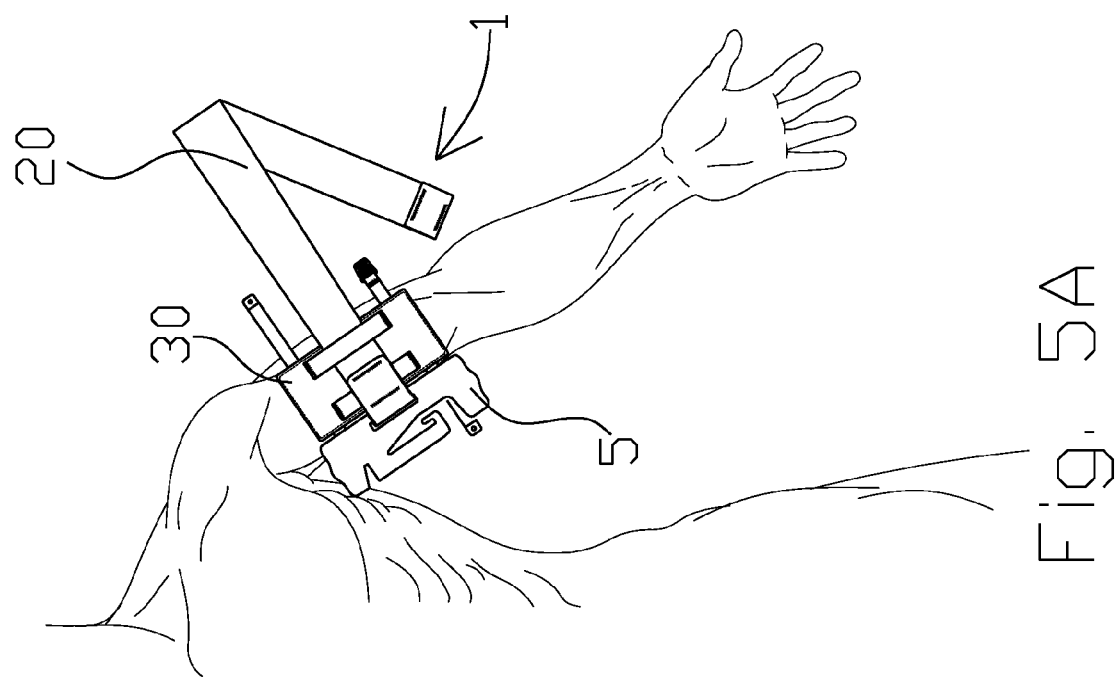

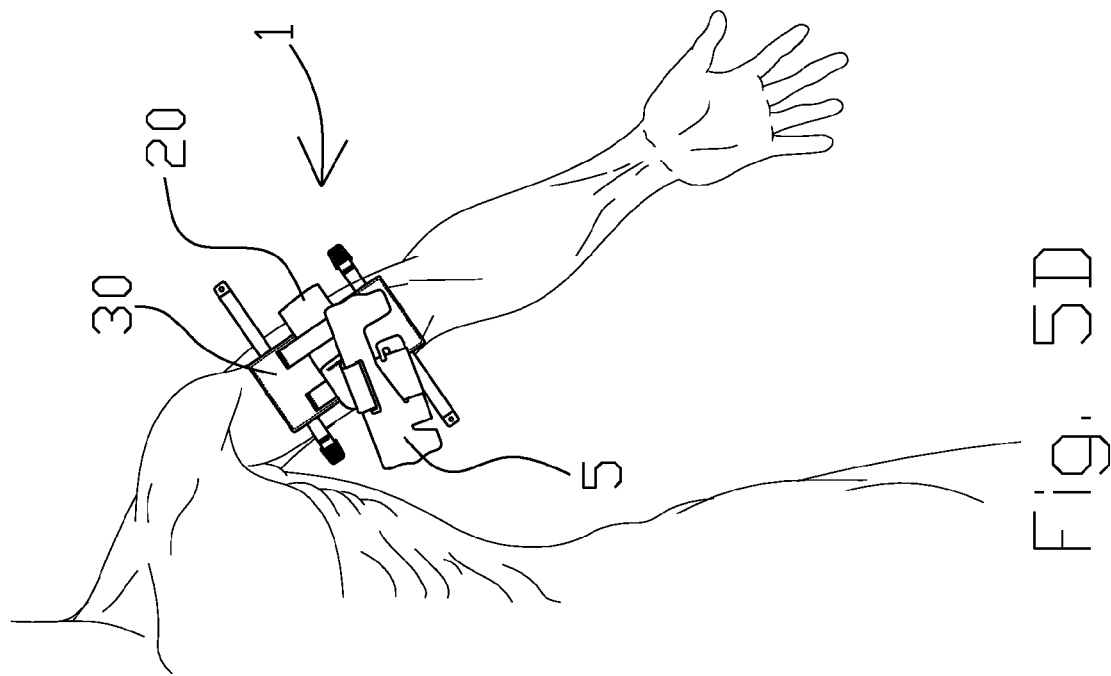
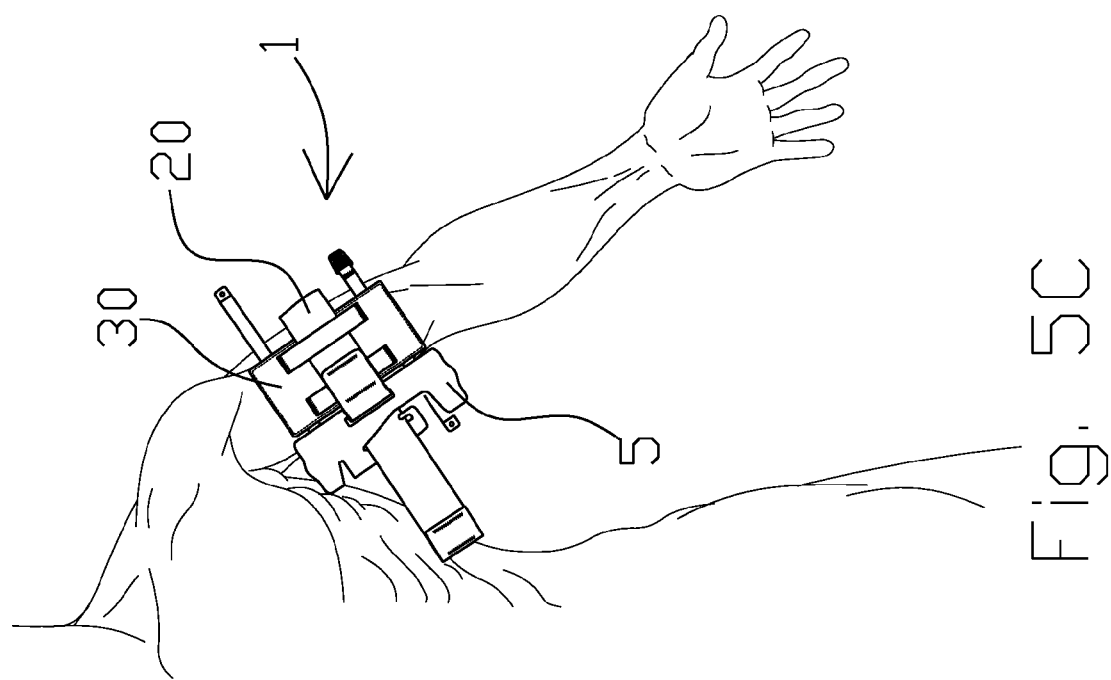

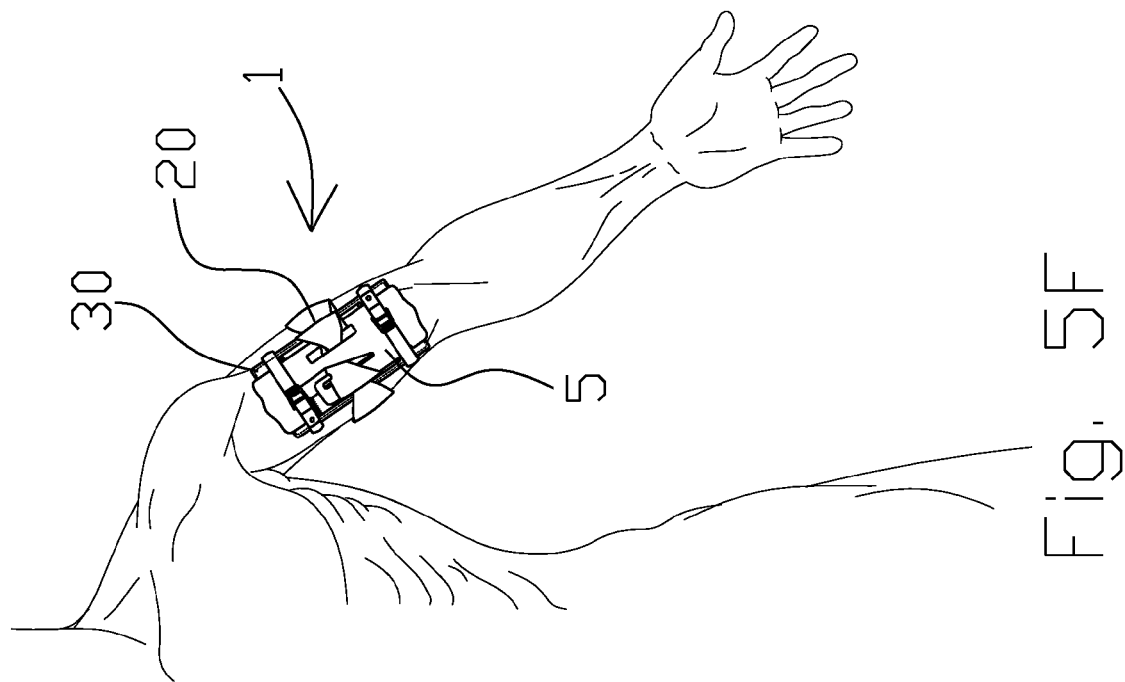
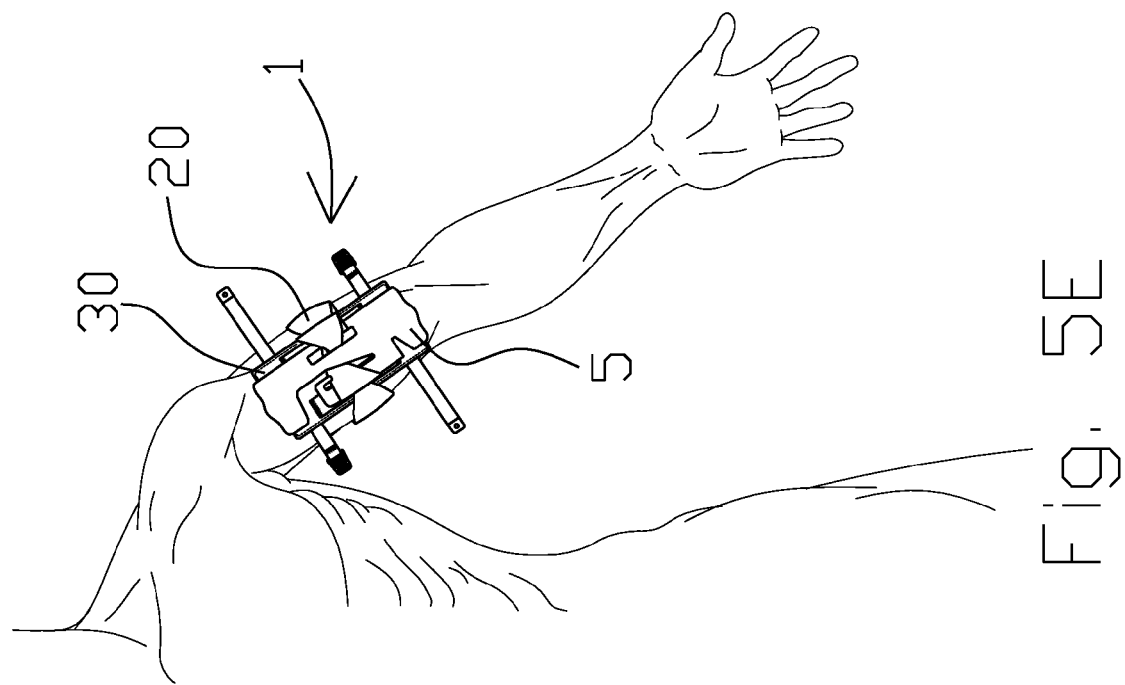

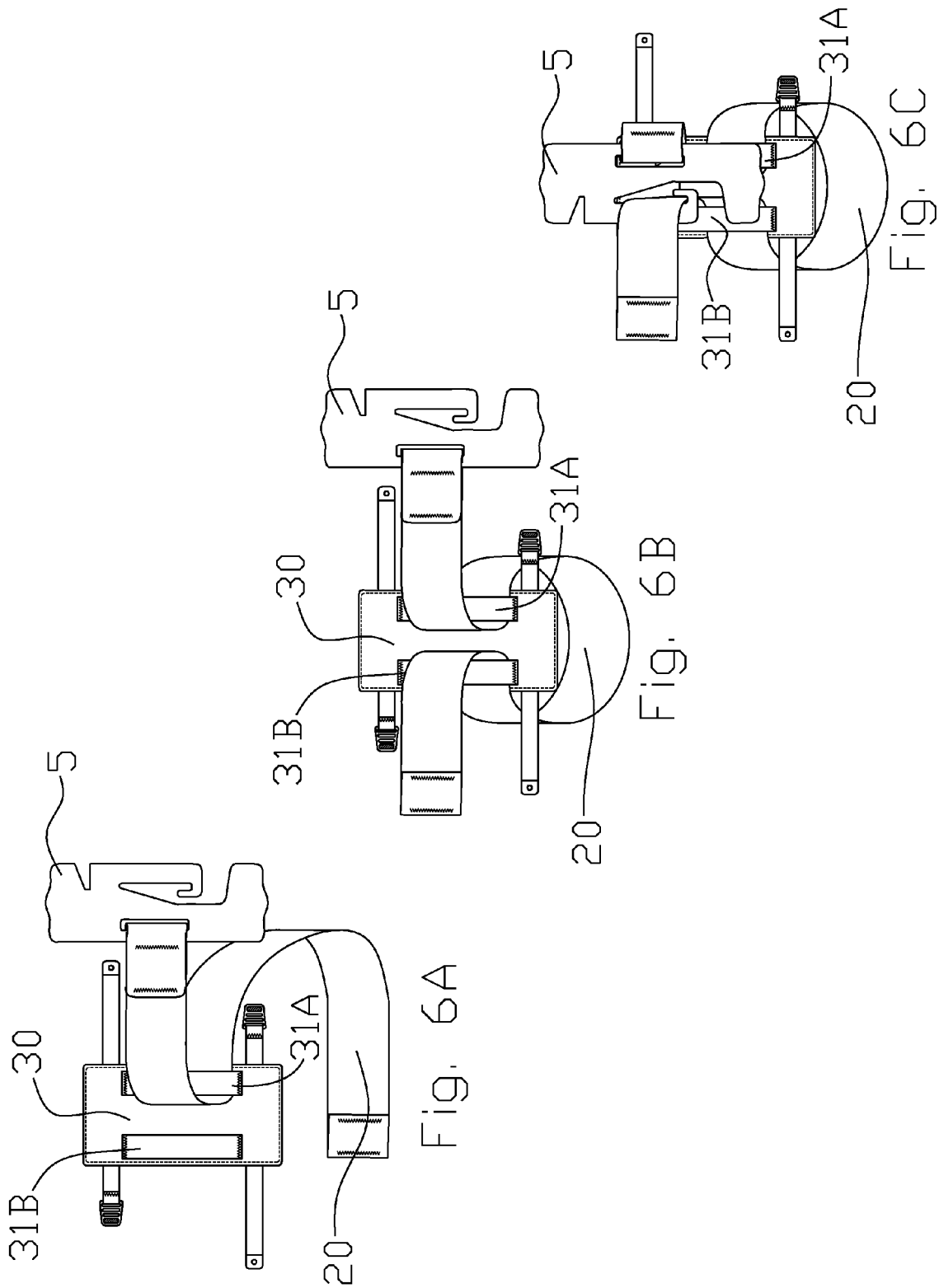

BATTLE APPLICATION TOURNIQUET FOR LIMB

The present invention relates to U.S. Provisional Patent Application Ser. No. 61/966,140 filed on Feb. 18, 2014 and claims priority therefrom.

The present application was not subject to federal research and/or development funding.

TECHNICAL FIELD

Generally, the invention relates to generally to a battlefield or emergency services medical devices and more specifically to a tourniquet having a buckle with an elongated strip of webbing attached thereto. Specifically, the invention is a tourniquet having a uniquely shaped buckle with an indentation that catches upon on edge of the strip of webbing to prevent the tourniquet from unwinding. In a further embodiment, the invention includes a base plate that communicates with the buckle and webbing to ensure a secure tourniquet.

BACKGROUND OF THE INVENTION

Tourniquets are used to stop blood flow to an injured region of a limb. Previously, tourniquets have comprised elongated materials which were wrapped around an injured limb to create a loop above the injured area and tightened, in a variety of manners, to restrict or stop blood flow into the injured area. If total blood flow is to be stopped, typically the materials must be tightened and maintained in place to achieve a successful tourniquet.

Tourniquets are commonly provided to military personnel and emergency medical personnel. Since an emergency can happen at any time, tourniquets should be designed for rapid use during the day and night. The present invention addresses these concerns and provides a tourniquet that is quick and easy to use in a variety of lighting conditions and may be deployed in a tactile manner or by feel alone. The following are representative of the state of art relating to tourniquets.

U.S. Pat. No. 2,113,534 to Brown discloses a tourniquet that consists of a pad secured to a strap in a position to extend beneath the buckle for preventing the latter from contacting with the skin of the person to whom the tourniquet is applied. The pad is provided with a slit in substantial alignment with the jaws of said buckle. The strap extends through the slit to hold said pad in position beneath said buckle. This construction effects a self-adjusting tourniquet buckle pad and assures that it is always in the correct position.

U.S. Pat. No. 2,468,133 to Sullivan discloses a tourniquet. The basic element of the tourniquet is a long rubber tube having closed ends and a structure similar to a bicycle tire inner tube. The tube is designed to be formed into a coil and to be inflated by way of a standard air valve.

U.S. Pat. No. 2,936,759 to Yuhas discloses a tourniquet. The tourniquet assembly in its entirety which comprises an elongated hollow tube, a buckle or fastening collar and a local pressure applying disc. The elongated hollow tube is formed of an elastic material such as vinyl chloride plastic and which contains a pre-injected gas. The ends are sealed to entrap the gas therein. The buckle or fastening collar is of cylindrical shape and preferably formed of sufficiently non-elastic material such as polyethylene plastic. The fastening collar is secured to one end of the tube by a self-locking arrangement including two longitudinally spaced apart apertures.

U.S. Pat. No. 3,504,675 to Bishop, Jr. discloses a disposable surgical tourniquet. A unitary, laminar assembly of plastic material forms a bladder for retaining air under suitable pressure to perform its tourniquet function. Sealed through the wall of the unitary body is a valve stem or the like communicating with the interior of the bladder for introducing suitable amounts of gas under pressure therein. When the cuff is to be used, it is convolutedly wound around a body member in a conventional manner with double-sided, pressure-sensitive tape disposed between the convolutions to hold them in place, and air or other gas then introduced at suitable pressure into the hollow interior portion of the cuff forming the bladder. The pressure-sensitive tape may extend substantially entirely across the bottom surface of the cuff, except for that portion thereof which may engage against the skin, and the fact that the tape engages entirely across the cuff and seals the overlapping convolutions together to assist in preventing relative side shifting of the convolutions.

U.S. Pat. No. 4,125,115 to Mayo et al. discloses a tourniquet. It has a semi-elastic belt fixed at one end to a tongue. The tongue is releasably engageable in a buckle. The other end of the belt passes through belt adjusting means to form a tourniquet loop. The belt adjusting means form part of the buckle. The length of the loop is adjustable as required. Slow and quick tourniquet release means are provided at the belt adjustment means and tongue engagement means, respectively.

U.S. Pat. No. 4,637,394 to Racz et al. discloses a constant pressure tourniquet. A constant pressure tourniquet has an interior chamber formed therein by a continuous wall surface. The wall of the tourniquet is made of an expansible elastomeric material. The chamber is inflated with a suitable fluid to a pressure in excess of the threshold pressure provided by the elastomeric material. The tourniquet preferably is of annular or rectangular configuration, and can be adjustably arranged to effectively form a toroidal void within which a pressure producing fluid is contained. The tourniquet is made in various different sizes and configurations, and includes overlapping marginal ends which are fastened together and thereby provides a suitable inside diameter for proper placement about one's limb, such as a finger, arm, or leg, for example. The physical characteristics exhibited by the elastomer are selected to provide the required internal pressure for preventing bleeding. The internal pressure and size of the tourniquet therefore is selected to prevent bleeding of that part of the anatomy that receives the tourniquet.

U.S. Pat. No. 7,776,064 to Jennifer et al. discloses a tourniquet article. The present invention relates generally to first aid articles and more specifically tourniquets. One embodiment of the claimed subject matter includes a tourniquet article comprising a base, a cap disposed on said base, a strap having one free end and one end attached to said base, a buckle attached to said base, a handle with an aperture to accommodate a portion of said strap, a ring attached to said base positioned adjacent to said base, wherein said tourniquet article is positioned around a limb, wherein said free end of said strap is pulled through both said ring and said handle aperture whereby said article is initially tightened around the limb, wherein said handle is turned until adequate pressure is applied to the limb, and wherein once adequate pressure is applied to the limb, one end of said handle is inserted into said ring to secure the tightened tourniquet in place. Another embodiment includes a safety screw disposed in said buckle, wherein said screw is tightened to prevent said strap from slipping. Another embodiment has a ring that is movable along the base. Another embodiment of the tourniquet article further includes a second ring disposed on said base positioned adjacent to said buckle.

U.S. Pat. No. 7,947,061 to Reis discloses a ratcheting tourniquet apparatus. A ratcheting tourniquet apparatus has a quick adjustment mechanism for initial tourniquet strap approximation, and a ratcheting assembly for fine, stringent strap adjustment about a limb of a patient. The apparatus provides for quick and easy use, even to the uninitiated. The apparatus provides for sufficient leverage via the ratcheting assembly such that severe tightening of the strap is possible as needed. The apparatus quick adjustment mechanism further provides instant tourniquet release.

SUMMARY OF THE INVENTION

The present invention provides a tourniquet comprising a buckle having a unique shape and including a strip of webbing attached to an edge of the buckle and utilizing a closed loop system to rapidly and easily restrict blood flow to a patient's limb. The buckle comprises a pair of notches on a first edge. One notch is centrally located and includes a J-hook into which the free end of the strip of webbing passes to complete a loop around an injured limb. An elongated opening is provided substantially near the second edge for receiving and fastening a fixed end of the strip of webbing. The tourniquet may further include a base plate having a pair of smaller strips of webbing attached thereto. A ladder-lock or double bar buckle is included on a free end of each of the smaller strips of webbing. In this manner, the base plate may be arranged on a back side of an injured limb and the smaller strips of webbing fastened across the buckle to maintain the tourniquet tightly around the injured limb. Bulbous regions are provided at opposite ends of the buckle, ie. the top and bottom ends.

In another aspect of the present invention a method of restricting blood flow is provided including providing a tourniquet of the present invention, placing the limb of a patient through the closed loop, depositing a portion of the strip of webbing within a first hooked opening in the buckle and pulling the end of the strip of webbing until loop is tightened and thereafter twisting the buckle until blood flow is further restricted, and inserting a tip created by second hooked opening arranged on the same side of the buckle as the first hooked opening beneath an edge of the loop.

It is an object of the invention to provide a tourniquet that may be single-handedly applied to an injured limb.

It is further object of the invention to provide a tourniquet that may be intuitively applied to an injured limb without any training.

It is an object of the invention to provide an adjustable tourniquet that may be easily applied to an injured limb in a variety of lighting conditions.

It is an object of the invention to provide a tourniquet having a base plate with a pair of small straps which may be arranged behind a back side of an injured limb and fastened to secure the buckle fixedly above the injury.

Additional objects and advantages of the invention will be set forth in part in the description which follows, and in part will be obvious from the description, or may be learned from practicing the invention. The objects and advantages of the invention will be obtained by means of instrumentalities in combinations particularly pointed out in the appended claims.

BRIEF DESCRIPTION OF THE DRAWINGS

FIG. 1A shows a perspective view of a buckle. FIG. 1B shows a view of a first embodiment of the invention wherein a strap attaches to the buckle via an elongated opening.

FIG. 2A shows a front side of a first embodiment of the base plate. FIG. 2B shows a backside of the base plate shown in FIG. 2A. FIG. 2C shows a front side of a second embodiment of the base plate. FIG. 2D shows a backside of the base plate shown in FIG. 2C. FIG. 2E shows the straps of the back plate fastened atop the buckle.

FIG. 3 shows a perspective view of a second embodiment of the invention including a base plate.

FIGS. 4A-4F show the application of the first embodiment of the tourniquet to an arm.

FIGS. 5A-5F show the application of the second embodiment of the tourniquet to an arm.

FIGS. 6A-6C show the self-application of the tourniquet to an arm using a technique wherein the loop is created and slid over the injured arm or limb.

DETAILED DESCRIPTION OF THE INVENTION

Figure 4D:
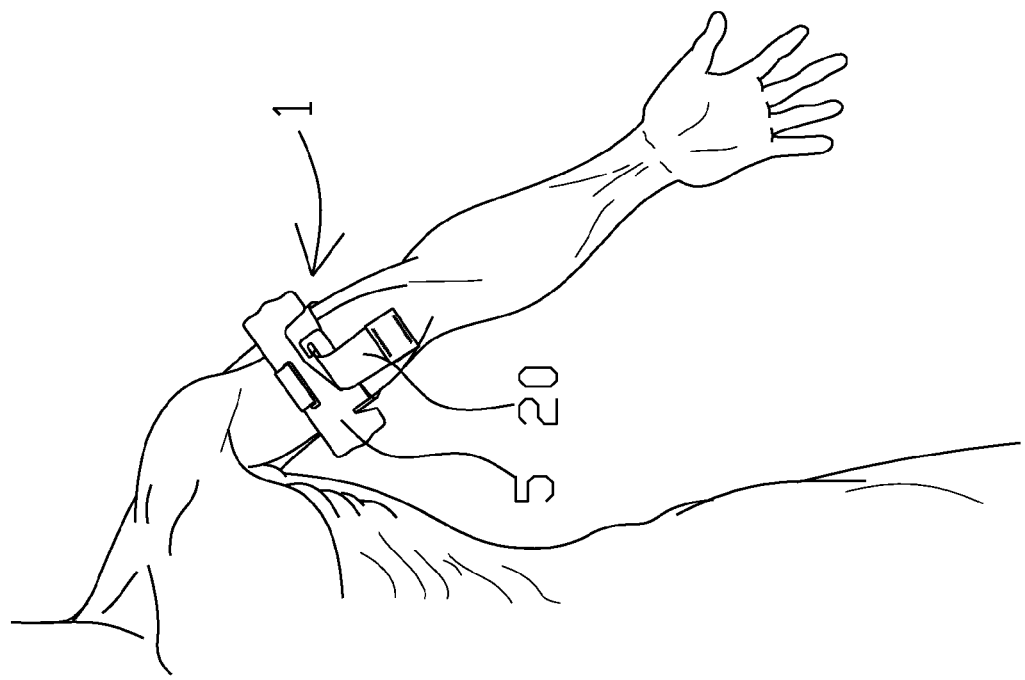

The embodiments of the invention and the various features and advantageous details thereof are more fully explained with reference to the non-limiting embodiments and examples that are described and/or illustrated in the accompanying drawings and set forth in the following description. It should be noted that the features illustrated in the drawings are not necessarily drawn to scale, and the features of one embodiment may be employed with the other embodiments as the skilled artisan recognizes, even if not explicitly stated herein. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims. Moreover, it is noted that like reference numerals represent similar parts throughout the several views of the drawings.

Figure 4C:
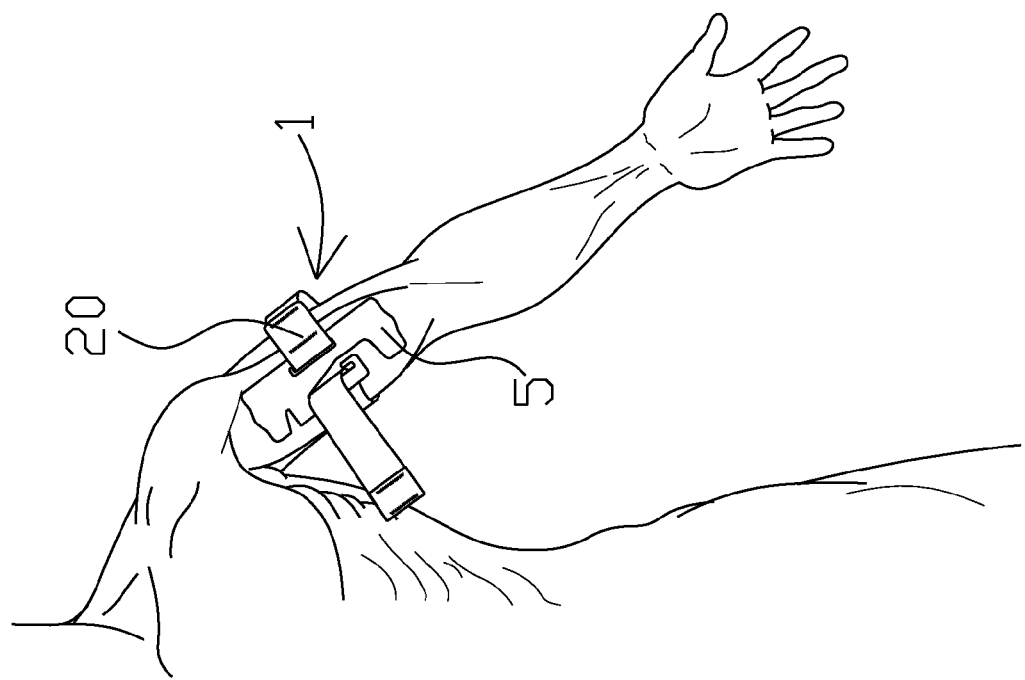
Figure 4E:
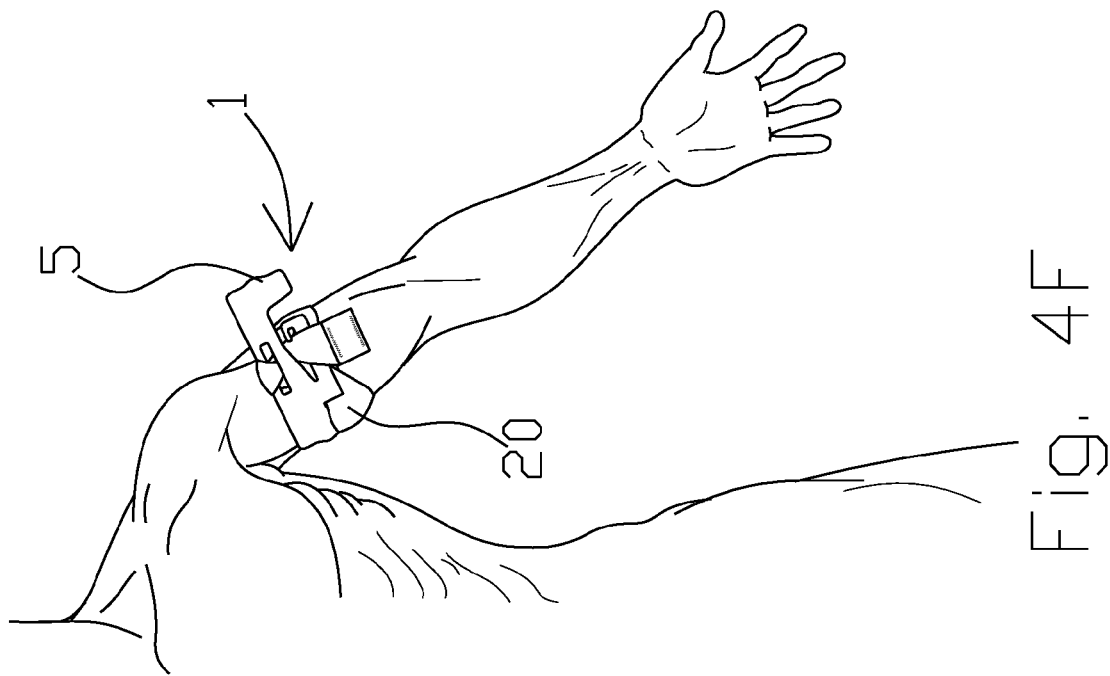
Figure 4F:
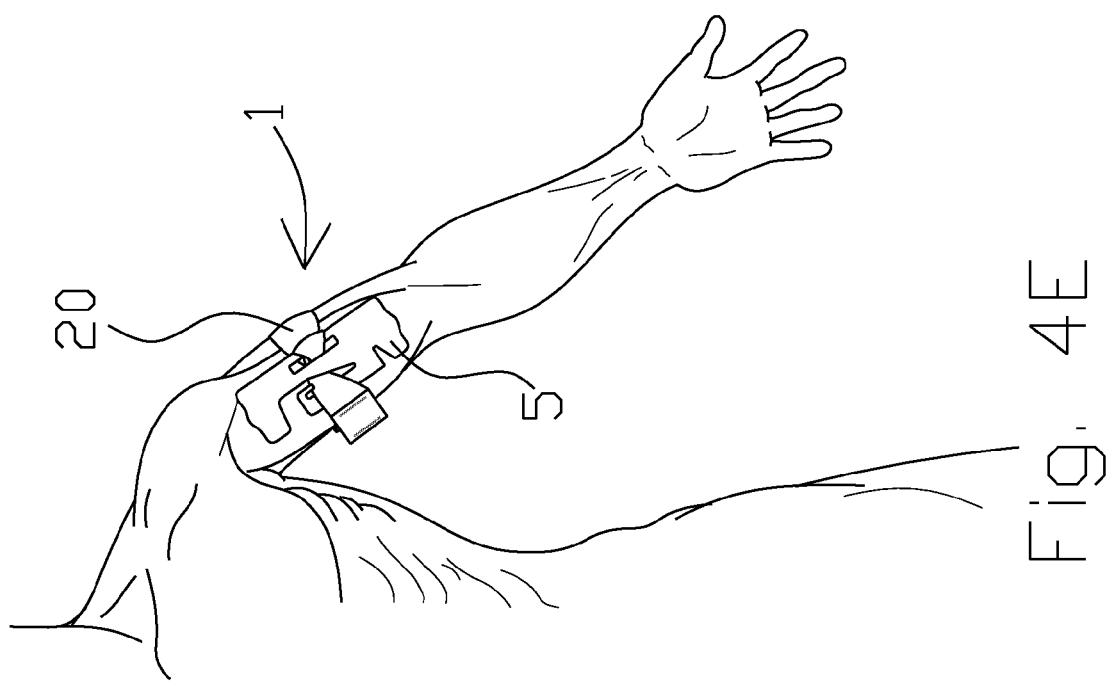

FIG. 1A shows a buckle 5 which comprises a pair of notches 11, 12 formed in a first side 10A. In the preferred embodiment, the buckle 5 is 5 inches long by 1.5 inches wide by 3/16 of an inch thick. Notch 11 comprises a channel 19 that extends upward from the first side 10A to terminate in an opening 18 into which a portion of strap 20 is seated, as more clearly shown in the FIGS. 4C, 5C, and 6C. The channel 19 includes a sloped edge 15 having a rounded corner that extends to a straight edge 16. Straight edge 16 is substantially parallel to sides 10A, 10B and is substantially 2" long and 5/16" wide. Upward extension 17 forms a generally J-hook shape as shown. The channel 19 defined between upward extension 17 and the interior portion of the buckle is 1/8" wide. The upward extension is substantially 1/8" long. Notch 12 is formed by a straight edge that is perpendicular to side 10A and terminates in a rounded corner that extends into a sloped edge as shown. Notch 12 is substantially 1/2" deep. The rounded corner is 1/8" tapered. An elongated opening 13 is provided substantially near the second side 10B and extends in a lengthwise manner from the top towards the bottom of the buckle and is ⅛" wide by 2" long. The elongated opening 13 is formed substantially ⁵⁄₁₆" from the second side 10B. The elongated opening 13 receives an end of the strap 20 as more clearly shown in FIG. 1B. An end of the strap 20 is fed through the elongated opening 13 and folded back across itself and stitched with stitches 50 to secure the strap 20 to the buckle 5. The finished length of strap 20 is preferably 36" long by 2" wide. A first bulbous region 14A is provided at the top of the buckle. A second bulbous region 14B bulges from the bottom of the buckle. The bulbous regions 14A, 14B aid in gripping the buckle 5 when a tourniquet is applied to an injured limb.

FIGS. 2A, 2B show a back plate 30 formed from a rigid material 30 and overlapped with fabric 36 which is stitched thereto via stitches 50. Otherwise, the back plate 30 may be formed from a webbing material such as that comprising strap 20. Loops 38A, 38B are stitched to a front side of the back plate 30 for receiving the free end of the strap 20. A pair of smaller straps 32 is stitched to a back side of the back plate 30 as shown in FIG. 2B. Each strap includes a metal end 34 and a ladder lock 33 attached thereto. A second embodiment of the back plate 30 is shown in FIGS. 2C, 2D wherein the fabric 36 includes openings 31C on either side which forms a loop through which a free end of strap 20 is passed. FIG. 2E shows the second embodiment of the back plate 30 fastened to the buckle 5 via straps 32 in a stored position. The ends of the straps 32 may be disengaged from one another and the buckle 5 is loosened from the black plate 30 prior to installing the tourniquet 1 about an injured limb. FIG. 3 shows the tourniquet 1 assembled with the buckle 5 fastened to loop 13B via stitching 50 that creates a loop 65 which passes through both elongated opening 13 and loop 38B. The strip 20 also passes through loop 38A. In a preferred embodiment, the straps 32 are arranged ¼"-½+ from the top and bottom of the back plate 30 with substantially 2.5" of space between the two straps 32. Each strap is preferably 14" long and formed from ¾" webbing. The overall size of the back plate is preferably 10" long by 2" wide.

FIGS. 4A-4F show the application of a tourniquet 1 being applied to an injured arm. In this instance, the tourniquet is arranged on injured limb 2-3 inches above injury. The strap 20 is wrapped about the injured limb and slid through channel 19 and into opening 18. The user should ensure that the entire width of strap 20 is in opening 18. If no back plate is included, padding should be placed between the buckle 5 and the user's skin. This step is not required for using the tourniquet but will decrease pain or tissue damage from the twisting pinch point. The strap 20 is tightened and the buckle 5 is then twisted until the injury stops bleeding. The buckle 5 is then secured in place by sliding an edge of the strap 20 into one of either notch 11, 12 and tucking a portion of buckle 5 under the strap. The buckle should begrasped and twisted at least two times to completely shutoff blood flow to the injured area.

The tourniquet may also be applied with one hand as shown in FIGS. 5A-5F. During one handed application of the tourniquet, the back plated is placed on the arm, if one is present. Next, the strap 20 is wrapped around injured limb 2-3 inches above the injury. Strap 20 is through notch 12 and the steps mentioned above are repeated. Once the bleeding has stopped, buckle 5 is then secured in place. Each of the pair of smaller straps 32 is secured about the buckle 5 by passing metal end 34 and through ladder lock 33 and pulling the smaller straps 32 tight.

The tourniquet 1 may be preloaded with a loop such that it may be slid over the injured area of the limb as shown in FIGS. 6A-6C. In this instance, strap 20 is passed though one of the openings on the back of the back plate 30. Then strap 20 is slid through notch 12 and into opening 18 such that tourniquet 1 is preloaded so it may be easily passed over an injured limb. This loop is slid over the limb and tightened 2-3 inches above the injury. The above recited steps are then repeated.

It is to be understood that the invention is not limited to the exact construction illustrated and described above, but that various changes and modifications may be made without departing from the spirit and the scope of the invention as defined in the following claims. While the invention has been described with respect to preferred embodiments, it is intended that all matter contained in the above description or shown in the accompanying drawings shall be interpreted as illustrative and not in limiting sense. From the above disclosure of the general principles of the present invention and the preceding detailed description, those skilled in the art will readily comprehend the various modifications to which the present invention is susceptible. Therefore, the scope of the invention should be limited only by the following claims and equivalents thereof.

I claim:

1. A tourniquet comprising:
a buckle having a first and second notch formed in a first side, said first notch comprising a channel that extends upward from the first side to terminate in an opening, said channel including a sloped edge terminating in a rounded corner that extends to a straight edge that is substantially parallel to the first side, an upward extension forming a generally J-hook at an end of the straight edge opposite said rounded corner, said second notch formed by a straight edge that is perpendicular to the first side and terminating in a rounded corner that extends into a sloped edge, an elongated opening formed substantially near a second side and extending in a lengthwise manner from a top towards a bottom of the buckle, a first bulbous region provided at the top of the buckle, a second bulbous region formed in the bottom of the buckle, said first and second bulbous regions aiding in gripping the buckle when the tourniquet is applied to an injured limb; and,
a strip of webbing having a first end and a second end, said second end comprising a permanent loop attached to the elongated opening in the buckle; wherein said elongated opening of the buckle receives an end of the strip of webbing such that an end of the strap is fed through the elongated opening and folded back across itself and stitched to secure the strap to the buckle,
wherein said strip of webbing is inserted into the channel to be seated between the J-hook and the rounded corner of the channel.

2. The tourniquet of claim 1 further comprising a back plate having at least one loop through which the strip of webbing is fed and a pair of straps fastened to a back side of the back plate, each of said straps including a fastener attached thereto.

3. The tourniquet of claim 2 wherein said a back plate is formed from a rigid material and overlapped with fabric which is stitched thereto.

4. The tourniquet of claim 2 wherein the back plate is formed from webbing material and having loops stitched to a front side of the back plate for receiving a free end of the strip of webbing.

5. The tourniquet of claim 2 wherein each of said pair of straps includes a metal end and a ladder lock attached thereto.

6. The tourniquet of claim 2 wherein said back plate includes openings on either side which forms a loop through which a free end of strap is passed.

7. A tourniquet comprising:
   a buckle having a first and second notch formed in a first side, said first notch comprising a channel that extends upward from the first side to terminate in an opening, said channel including a sloped edge terminating in a rounded corner that extends to a straight edge that is substantially parallel to the first side, an upward extension forming a generally J-hook at an end of the straight edge opposite said rounded corner, said second notch formed by a straight edge that is perpendicular to the first side and terminating in a rounded corner that extends into a sloped edge, an elongated opening formed substantially near a second side and extending in a lengthwise manner from a top towards a bottom of the buckle, a first bulbous region provided at the top of the buckle, a second bulbous region formed in the bottom of the buckle, said first and second bulbous regions aiding in gripping the buckle when the tourniquet is applied to an injured limb;
   a strip of webbing having a first end and a second end, said second end comprising a permanent loop attached to the elongated opening in the buckle; and,
   a back plate having at least one loop through which the strip of webbing is fed and a pair of straps fastened to a back side of the back plate, each of said straps including a fastener attached thereto
   wherein said elongated opening of the buckle receives an end of the strip of webbing such that an end of the strap is fed through the elongated opening and folded back across itself and stitched to secure the strap to the buckle, and
   wherein said strip of webbing is inserted into the channel to be seated between the J-hook and the rounded corner of the channel.

8. The tourniquet of claim 7 wherein said a back plate is formed from a rigid material and overlapped with fabric which is stitched thereto.

9. The tourniquet of claim 7 wherein the back plate is formed from webbing material and having loops stitched to a front side of the back plate for receiving a free end of the strip of webbing.

10. The tourniquet of claim 7 wherein each of said pair of straps includes a metal end and a ladder lock attached thereto.

11. The tourniquet of claim 7 wherein said back plate includes openings on either side which forms a loop through which a free end of strap is passed.

* * * * *